United States Patent
Kirenko et al.

(10) Patent No.: US 10,052,038 B2
(45) Date of Patent: *Aug. 21, 2018

(54) DEVICE AND METHOD FOR DETERMINING VITAL SIGNS OF A SUBJECT

(71) Applicant: KONINKLIJKE PHILIPS N.V., Eindhoven (NL)

(72) Inventors: Ihor Olehovych Kirenko, Eindhoven (NL); Albertus Cornelis Den Brinker, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1127 days.

This patent is subject to a terminal disclaimer.

(21) Appl. No.: 14/200,622

(22) Filed: Mar. 7, 2014

(65) Prior Publication Data
US 2014/0276099 A1    Sep. 18, 2014

Related U.S. Application Data

(60) Provisional application No. 61/781,269, filed on Mar. 14, 2013.

(30) Foreign Application Priority Data

Mar. 14, 2013  (EP) .................................. 13159173

(51) Int. Cl.
*A61B 5/024* (2006.01)
*A61B 5/00* (2006.01)
*G06T 7/00* (2017.01)

(52) U.S. Cl.
CPC ........ *A61B 5/02416* (2013.01); *A61B 5/0077* (2013.01); *A61B 5/7221* (2013.01);
(Continued)

(58) Field of Classification Search
CPC .............. A61B 5/02416; A61B 5/7235; A61B 5/14551; A61B 5/14552
See application file for complete search history.

(56) References Cited

U.S. PATENT DOCUMENTS 8,768,424 B2    7/2014 Crowe
2009/0226071 A1*   9/2009 Schuler .............. A61B 5/02416
                                                 382/133
(Continued)

FOREIGN PATENT DOCUMENTS

JP    59160446    9/1984
JP    2172443    7/1990
(Continued)

OTHER PUBLICATIONS

Verkruysse et al. ("Remote Plethysmographic Imaging Using Ambient Light"); provided on IDS.*
(Continued)

*Primary Examiner* — Alyssa M. Alter (57) ABSTRACT

A device for determining a vital sign of a subject comprises an interface that receives a data stream derived from detected electromagnetic radiation reflected from a region of interest including a skin area of the subject, said data stream comprising a data signal per skin pixel area of one or more skin pixels for a plurality of skin pixel areas of said region of interest, a data signal representing the detected electromagnetic radiation reflected from the respective skin pixel area over time. An analyzer analyzes spatial and/or temporal properties of the skin area. A processor determines a vital sign information signal of the subject based on the data signals of skin pixel areas within the skin area, and a post-processor determines the desired vital sign from said vital sign information signal, wherein said determined spatial and/or temporal properties are used by the processor for
(Continued)

determining the vital sign information signal and/or by the post-processor for determining the desired vital sign.

20 Claims, 2 Drawing Sheets

(52) U.S. Cl.
CPC .......... *A61B 5/7235* (2013.01); *G06T 7/0016* (2013.01); *A61B 5/725* (2013.01); *G06T 2207/10016* (2013.01); *G06T 2207/10024* (2013.01); *G06T 2207/20021* (2013.01); *G06T 2207/30076* (2013.01)

(56) References Cited

U.S. PATENT DOCUMENTS

| | | |
|---|---|---|
| 2012/0195469 A1 | 8/2012 | Kirenko et al. |
| 2012/0203080 A1 | 8/2012 | Kim et al. |
| 2012/0212631 A1 | 8/2012 | Kirenko et al. |
| 2013/0294505 A1 | 11/2013 | Kirenko et al. |
| 2014/0031696 A1 | 1/2014 | Schmeitz et al. |
| 2014/0303454 A1 | 10/2014 | Clifton et al. |

FOREIGN PATENT DOCUMENTS

| | | |
|---|---|---|
| JP | 2006102159 | 4/2006 |
| WO | 2010001248 A2 | 1/2010 |
| WO | 2012093320 A2 | 7/2012 |
| WO | 2012143842 A2 | 10/2012 |
| WO | 2013027027 A2 | 2/2013 |

OTHER PUBLICATIONS

Karlen, W., et al.; Photoplethysmogram signal quality estimation using repeated Gaussian filters and cross-correlation; 2012; Physiological Measurement; 33(10)1617-1629.

Singh, M., et al.; Spatial texture analysis: a comparative study; 2002; Pattern Recognition; vol. 1; pp. 676-679.

Tsouri, G. R., et a.; Constrained independent component analysis approach to nonobtrusive pulse rate measurements; 2012; Journal of Biomedical Optics; 17(7)077011-1.

Verkruysse, W., et al.; Remote plethysmographic imaging using ambient light; 2008; Optical Express; 16(26) 21434-21445.

Wieringa, F. P., et al.; Contactless Multiple Wavelength Photoplethysmographic Imaging: A First Step Toward"SpO2 Camera" Technology; 2005; Annals of Biomedical Engineering; 33(8)1034-1041.

* cited by examiner

FIG.1

FIG.2

DEVICE AND METHOD FOR DETERMINING VITAL SIGNS OF A SUBJECT

CROSS REFERENCE TO RELATED APPLICATIONS

This application claims the benefit of U.S. provisional application Ser. No. 61/781,269 filed Mar. 14, 2013 and European provisional application serial no. 13159173.7 filed Mar. 14, 2013, both of which are incorporated herein by reference.

FIELD OF THE INVENTION

The present invention relates to a device and a method for determining the vital signs of a subject. In particular, the present invention relates to an unobtrusive optical measurement approach which can be used for detecting vital signs in an observed subject, such as a person or animal. In this context, optical measurement refers to remote photoplethysmography (R-PPG).

BACKGROUND OF THE INVENTION

Vital signs of a person, for example the heart rate (HR), the respiration rate (RR) or the blood oxygen saturation, serve as indicators of the current state of a person and as powerful predictors of serious medical events. For this reason, vital signs are extensively monitored in inpatient and outpatient care settings, at home or in further health, leisure and fitness settings.

One way of measuring vital signs is plethysmography. Plethysmography generally refers to the measurement of volume changes of an organ or a body part and in particular to the detection of volume changes due to a cardio-vascular pulse wave traveling through the body of a subject with every heart beat.

Photoplethysmography (PPG) is an optical measurement technique that evaluates a time-variant change of light reflectance or transmission of an area or volume of interest. PPG is based on the principle that blood absorbs light more than surrounding tissue, so variations in blood volume with every heart beat affect transmission or reflectance correspondingly. Besides information about the heart rate, a PPG waveform can comprise information attributable to further physiological phenomena such as the respiration. By evaluating the transmissivity and/or reflectivity at different wavelengths (typically red and infrared), the blood oxygen saturation can be determined.

Conventional pulse oximeters for measuring the heart rate and the (arterial) blood oxygen saturation (also called SpO2) of a subject are attached to the skin of the subject, for instance to a finger tip, earlobe or forehead. Therefore, they are referred to as 'contact' PPG devices. A typical pulse oximeter comprises a red LED and an infrared LED as light sources and one photodiode for detecting light that has been transmitted through patient tissue. Commercially available pulse oximeters quickly switch between measurements at a red and an infrared wavelength and thereby measure the transmissivity of the same area or volume of tissue at two different wavelengths. This is referred to as time-division-multiplexing. The transmissivity over time at each wavelength gives the PPG waveforms for red and infrared wavelengths. Although contact PPG is regarded as a basically non-invasive technique, contact PPG measurement is often experienced as being unpleasant, since the pulse oximeter is directly attached to the subject and any cables limit the freedom to move.

Recently, non-contact, remote PPG (R-PPG) devices for unobtrusive measurements have been introduced. Remote PPG utilizes light sources or, in general radiation sources, disposed remotely from the subject of interest. Similarly, also a detector, e.g., a camera or a photo detector, can be disposed remotely from the subject of interest. Therefore, remote photoplethysmographic systems and devices are considered unobtrusive and well suited for medical as well as non-medical everyday applications. However, remote PPG devices typically achieve a lower signal-to-noise ratio.

Verkruysse et al., "Remote plethysmographic imaging using ambient light", Optics Express, 16(26), 22 Dec. 2008, pp. 21434-21445 demonstrates that photoplethysmographic signals can be measured remotely using ambient light and a conventional consumer level video camera.

Wieringa, et al., "Contactless Multiple Wavelength Photoplethysmographic Imaging: A First Step Toward "SpO2 Camera" Technology," Ann. Biomed. Eng. 33, 1034-1041 (2005), discloses a remote PPG system for contactless imaging of arterial oxygen saturation in tissue based upon the measurement of plethysmographic signals at different wavelengths. The system comprises a monochrome CMOS-camera and a light source with LEDs of three different wavelengths. The camera sequentially acquires three movies of the subject at the three different wavelengths. The pulse rate can be determined from a movie at a single wavelength, whereas at least two movies at different wavelengths are required for determining the oxygen saturation. The measurements are performed in a darkroom, using only one wavelength at a time.

Using remote PPG technology, vital signs can be measured from video camera signals, as it is revealed by minute light absorption changes in the skin caused by the pulsating blood volume. As this signal is very small and hidden in much larger variations due to illumination changes and motion, there is a general interest in improving the fundamentally low signal-to-noise ratio (SNR). There still are demanding situations, with severe motion, challenging environmental illumination conditions, or high required accuracy of the application, where an improved robustness of the remote PPG devices and methods are required.

SUMMARY OF THE INVENTION

It an object of the present invention to provide an improved device and method for determining vital signs of a subject having an increased signal-to-noise ratio and efficiency in reduction of artefacts caused by motion of the subject.

In a first aspect of the present invention a device for determining vital signs of a subject is presented, the device comprising:

an interface that receives a data stream derived from detected electromagnetic radiation reflected from a region of interest including a skin area of the subject, said data stream comprising a data signal per skin pixel area of one or more skin pixels for a plurality of skin pixel areas of said region of interest, a data signal representing the detected electromagnetic radiation reflected from the respective skin pixel area over time, an analyzer that analyzes spatial and/or temporal properties of the skin area, a processor that determines a vital sign information signal of the subject based on the data signals of skin pixel areas within the skin area, and a post-processor that determines the desired vital sign from said vital sign information signal, wherein said determined spatial and/or temporal properties are used by the processor for determining the vital sign information signal and/or by the post-processor for determining the desired vital sign.

In a further aspect of the present invention a corresponding method for determining the blood oxygen saturation of a subject is presented, the method comprising:

receiving a data stream derived from detected electromagnetic radiation reflected from a region of interest including a skin area of the subject, said data stream comprising a data signal per skin pixel area of one or more skin pixels for a plurality of skin pixel areas of said region of interest, a data signal representing the detected electromagnetic radiation reflected from the respective skin pixel area over time, analyzing spatial and/or temporal properties of the skin area, determining a vital sign information signal of the subject based on the data signals of skin pixel areas within the skin area, and determining the desired vital sign from said vital sign information signal, wherein said determined spatial and/or temporal properties are used for determining the vital sign information signal and/or by the post-processor for determining the desired vital sign.

In yet further aspects of the present invention, there are provided a computer program which comprises program code means for causing a computer to perform the steps of the method when said computer program is carried out on a computer as well as a non-transitory computer-readable recording medium that stores therein a computer program product, which, when executed by a computer processor, causes the method disclosed herein to be performed.

Preferred embodiments of the invention are defined in the dependent claims. It shall be understood that the claimed method, computer program and medium have similar and/or identical preferred embodiments as the claimed device and as defined in the dependent claims.

According to the present invention an improvement of the extracted vital sign is achieved by an analysis of the spatial and/or temporal properties of the skin area used for extraction of the desired vital sign signal, in particular of a temporal consistency and/or a spatial analysis of the smoothness of the skin area. For instance, the spatial uniformity of the detected skin area is determined (e.g. measured or estimated) and/or the difference in the size and uniformity of the skin area between adjacent image frames is determined (e.g. measured or estimated). The determined information about the temporal and/or spatial properties of the skin area, in particular about spatial uniformity and temporal consistency of the skin area, is used to adjust one or more parameters and/or an algorithm used for extraction and/or post-processing, in particular for determining the vital sign information signal and/or for determining the desired vital sign, or to select a post-processing method which is the most optimal for the determined spatial and/or temporal properties of the skin area. Thus, the signal-to-noise ratio and the efficiency in reduction of artefacts caused by motion of a subject can be efficiently improved.

Spatial properties of a skin area include, but not limited to dynamic range of spatial blocks, spatial texture, color uniformity and variance or entropy of pixel values. Spatial properties can be part of temporal properties as well. For instance, dynamic range as well as a temporal consistency of the dynamic range can be used as spatial and temporal properties.

The interaction of electromagnetic radiation, in particular light, with biological tissue is complex and includes the (optical) processes of (multiple) scattering, backscattering, absorption, transmission and (diffuse) reflection. The term "reflect" as used in the context of the present invention is not to be construed as limited to specular reflection but comprises the afore-mentioned types of interaction of electromagnetic radiation, in particular light, with tissue and any combinations thereof.

The term "vital sign" as used in the context of the present invention refers to a physiological parameter of a subject (i.e. a living being) and derivative parameters. In particular, the term "vital sign" comprises heart rate (HR) (sometimes also called pulse rate), heart rate variability (pulse rate variability), pulsatility strength, perfusion, perfusion indicator, perfusion variability, Traube Hering Mayer waves, respiratory rate (RR), body temperature, blood pressure, a concentration of a substance in blood and/or tissue, such as (arterial) blood oxygen saturation or glucose level.

The term "vital sign information" as used in the context of the present invention comprises the one or more measured vital signs as defined above. Furthermore, it comprises data referring to a physiological parameter, corresponding waveform traces or data referring to a physiological parameter of a time that can serve for subsequent analysis.

For obtaining a vital sign information signal of the subject the data signals of skin pixel areas within the skin area are evaluated. Here, a "skin pixel area" means an area comprising one skin pixel or a group of adjacent skin pixels, i.e. a data signal may be derived for a single pixel or a group of skin pixels.

In an embodiment said analyzer is configured to determine the smoothness, size, uniformity of the skin area and/or of chrominance and/or luminance components of the skin area over time. Thus, one or more parameters of the skin area can be exploited. Generally, smoothness represents more a high-frequency property, while uniformity is an indication of an equal DC-level. Smooth areas might still be non-uniform due to a presence of smooth transition in pixel values.

There are generally several methods for determine the spatial uniformity of the skin area and its stability over time. According to another embodiment said analyzer is configured to determine the spatial uniformity of the skin area over time by dividing the skin area into skin pixel blocks (comprising a group of skin pixels), determining the spatial uniformity of said skin pixel blocks and determining the number of smooth and/or textured smooth skin pixel blocks. Preferably, said analyzer is configured to determine the number of smooth and/or textured skin pixel blocks over time. Temporal changes of the number of smooth and/or textured skin pixel blocks can then be evaluated and used for adapting the (post-)processing of the data signals and/or the vital sign information signals to finally obtain the desired vital sign(s).

In another embodiment said analyzer is configured to determine reliability information from said spatial and/or temporal properties of the skin area, said reliability information indicating the reliability of the determination of vital sign information or vital sign determined based on the data signals of skin pixel areas within the skin area, wherein said processor and/or said post-processor is configured to use said reliability information for determining the vital sign information signal and/or by the post-processor for determining the desired vital sign. Thus, the accuracy of the desired vital sign can be further increased since additional knowledge about the determination of the vital sign information or the vital sign is additionally exploited so that e.g. rather unreliable vital sign information may be ignored or less weighted than very reliable vital sign information or vital sign.

The reliability information may be determined in different ways. In one way said analyzer is configured to determine said reliability information using the change of the number of smooth and/or textured skin pixel blocks over time and or the change of the size of the skin area over time. Preferably, said analyzer is configured to determine the reliability information to indicate a higher reliability the higher the number of smooth skin pixel blocks and larger the size of the skin area. Generally, the basic principle for adjustment of the (post-)processing is the following: the smoothness of a post-processing is increasing with a decrease of spatial uniformity of the skin area and/or an increase in its temporal instability.

For adapting the (post-)processing various options exist. In a preferred embodiment said post-processor is configured to set a temporal width and/or a time constant of a low-pass filter of said post-processor based on said determined spatial and/or temporal properties. In another said post-processor is configured to set a width of a band-pass filter of said post-processor based on said determined spatial and/or temporal properties. The choice of the preferred adjustment of post-processing depends on the requirements with respect to latency and accuracy of the determined vital sign. Changing the time constant of a filter to a higher value means more averaging over time which leads to a better signal-to-noise ratio (accuracy) at the cost of a slow response to changes (high latency).

Preferably, in an embodiment said post-processor is configured to update the determined vital sign only if the reliability information indicates a reliability above a predetermined reliability threshold. Thus, potentially wrong results of the determined vital sign are ignored and too strong changes of the vital sign (potentially caused by erroneous measurements) are avoided.

In another advantageous embodiment said processor is configured to rank skin pixel blocks of the skin area according to their associated temporal stability and to determine a vital sign information signal of the subject based on the data signals of skin pixels from the most temporally stable skin pixel blocks within the skin area. Alternatively or additionally said processor is configured to determine reliability weights for skin pixel blocks of the skin area according to their associated temporal stability and to determine a vital sign information signal of the subject based on the data signals of skin pixels, which are weighted according to the determined reliability weights of the associated skin pixel blocks. In this way the reliability of the vital sign determination can be further increased.

While the present invention generally works with data signals comprising a single data signal component in representative of a single spectral portion (e.g. in the spectral range of green light), in an embodiment said data signals comprise at least two data signal components, wherein a first data signal component is representative of a first spectral portion, in particular a visible-light portion, and wherein a second data signal component is representative of a second indicative spectral portion, in particular an infrared portion. This idea makes use of the fact that a penetration depth of radiation which is dependent on blood absorption and tissue absorption is basically also dependent on the wavelength of incident radiation. Typically, infrared (or near-infrared) and red light penetrates deeper into the subject's tissue than visible light having shorter wavelengths. By way of example, the first spectral portion can be formed of a band or sub-band in the green portion of visible radiation.

In a preferred embodiment the proposed device further comprises an imaging unit, in particular a camera, for remotely detecting electromagnetic radiation reflected from the subject, in particular in one or two different spectral ranges. The imaging unit is particularly suited for remote monitoring applications. The imaging unit can comprise one or more imaging elements. For instance, the imaging unit can comprise an array of photodiodes or charge-coupled devices. According to an embodiment, the imaging unit comprises at least two groups of imaging elements each of which is configured for detecting a single one of the data signal components. According to another embodiment, the imaging unit can make use of a single group of imaging elements having a response characteristic allowing for a detection of data signal components. The imaging unit can be further configured for capturing a sequence of image frames alternatingly representing the data signal components.

In another preferred embodiment the proposed device further comprises a radiation source, in particular a light source, for directing electromagnetic radiation to the subject, for instance in one or two different spectral ranges. The radiation source can be embodied by a broadband illumination source and/or can make use of a single group or two or even more groups of radiation elements. However, the proposed device does not necessarily have to comprise radiation source, but can also make use of ambient light sources which are not connected to the device.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1:
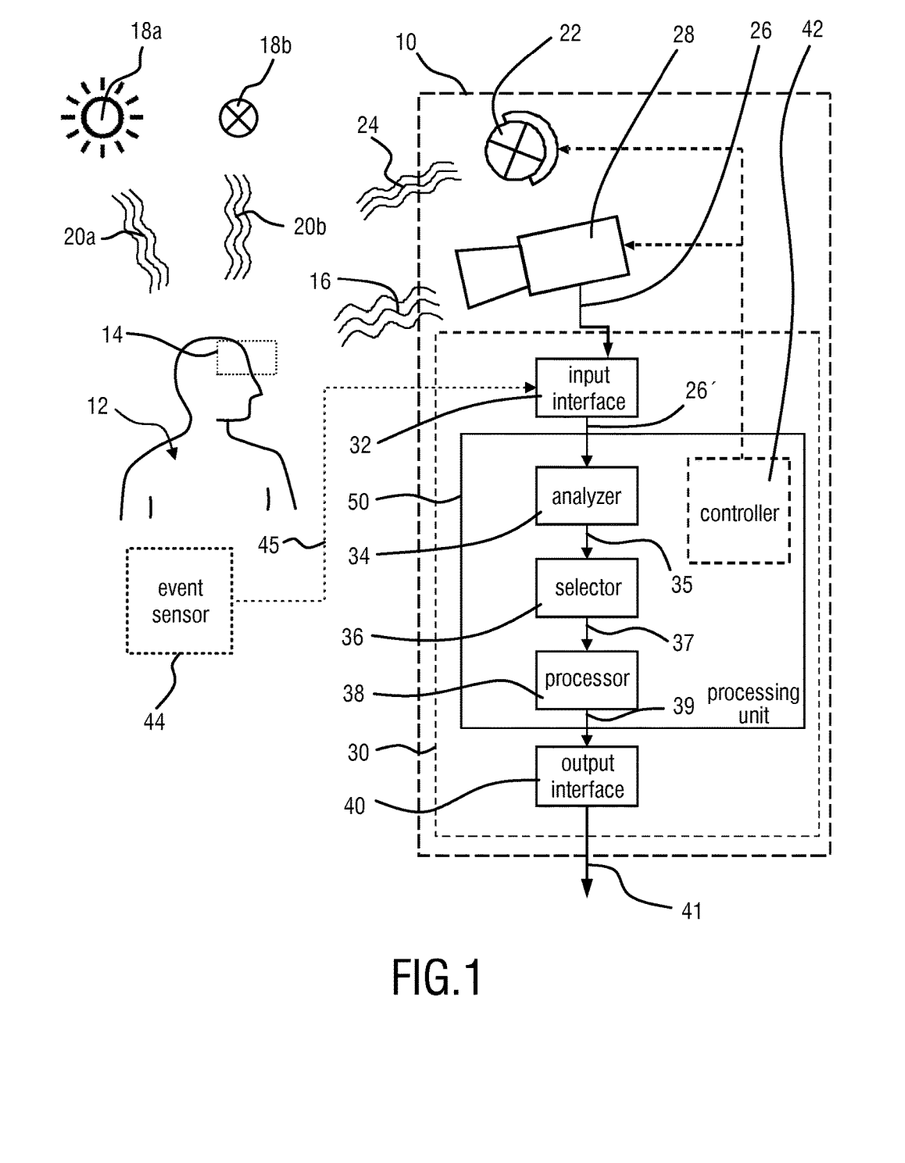
FIG. 1 shows a schematic diagram of a system in which a device according to the present invention is used.

FIG. 1 shows a schematic diagram of a system 10 in which a device 30 according to the present invention is used. The system 10 can be utilized for recording image frames representing a remote subject 12 or at least a portion 14 (a region of interest) of the subject 12 for remote PPG monitoring. The region of interest 14 comprises, by way of example, a forehead portion, a face portion or, more generally, one or more skin portions of the subject 12. The recorded data, for instance, a series of image frames, can be derived from electromagnetic radiation 16 reflected by the subject 12. Possibly, under certain conditions, at least part of the electromagnetic radiation could be emitted or transmitted by the subject 12 itself. Radiation transmission may occur when the subject 12 is exposed to strong illumination sources shining through the subject 12. Radiation emission may occur when infrared radiation caused by body heat is addressed and captured. However, for remote PPG applications, a huge portion of the electromagnetic radiation 16 to be captured can be considered radiation reflected by the subject 12. The subject 12 can be a human being or an animal, or, in general, a living being. Furthermore, the subject 12 can be considered a part of a human being highly indicative of a desired signal.

A source of radiation, such as sunlight 18*a*, an artificial radiation source 18*b* or a combination of several radiation sources, affects or impinges on the subject 12. The radiation sources 18*a*, 18*b* basically emit incident radiation 20*a*, 20*b* striking the subject 12. In addition, or in the alternative, the system 10 may also comprise or make use of an internal source 22 of electromagnetic radiation 24, which emits and directs incident radiation 24 to the subject 12 and which may also be part of the device 30 in an alternative embodiment. The internal source 22 of radiation 24 can be configured for directing radiation having defined characteristics to the subject 12, in particular radiation belonging to a defined spectral portion. Since in accordance with an embodiment of the invention, at least two distinct spectral portions are captured and processed, according to another aspect of this embodiment it is preferred that the internal source 22 of electromagnetic radiation 24 "matches" these spectral portions.

For extracting physiological information from the captured data, for instance, a sequence of image frames, radiation 16 from a defined part or portion of the subject 12, such as a the region of interest 14, is detected by an imaging unit 28. The imaging unit 28 can be embodied, by way of example, by an optical sensor means configured to capture information belonging to at least one spectral component of the electromagnetic radiation 16. In an embodiment, the imaging unit 28 is embodied by a camera or a set of cameras, such as a video camera (e.g. an RGB camera). The imaging unit 28 may also be part of the device 30 in an alternative embodiment.

Needless to say, the device 30 can also be adapted to process input signals, namely an input data stream 26, already recorded in advance and, in the meantime, stored or buffered. As indicated above, the electromagnetic radiation 16 can contain a continuous or discrete characteristic signal which can be highly indicative of at least one vital sign parameter 26, in the context of the present invention particularly the heart rate, respiration rate and/or blood oxygen saturation.

The device 30 for determining a vital sign of a subject according to the present invention comprises an (input) interface 32 for receiving the data stream 26 (from the imaging unit 28 or from a storage unit or buffer) derived from detected electromagnetic radiation 16 reflected (including emitted or transmitted radiation) from a region of interest 14 including a skin area of the subject 12. Said data stream 26 comprises a data signal per skin pixel for a plurality of skin pixel areas of one or more skin pixels (preferably for all skin pixel areas or even for all individual skin pixels) of said region of interest, wherein a data signal represents the detected electromagnetic radiation 16 reflected from the respective skin pixel area over time.

An analyzer 34 is provided for analyzing spatial and/or temporal properties of the skin area 14. Thus, information about the spatial and/or temporal properties of the skin area is output from the analyzer 34. In an embodiment, the analyzer computes relative amplitudes in a single spectral band (e.g. of green light) or in the red and infrared spectral band from the temporal skin reflectance represented by the data signals of the plurality of the skin pixels.

The device 30 further comprises a processor 36 for determining a vital sign information signal of the subject based on the data signals of skin pixel areas within the skin area and a post-processor 38 for determining the desired vital sign from said vital sign information signal. This way of processing the data signals is generally known in the art of remote PPG and shall thus not be explained in more detail here. Contrary to the known devices and methods, however, said determined spatial and/or temporal properties are used by the processor 36 for determining the vital sign information signal and/or by the post-processor 38 for determining the desired vital sign.

Finally, an (output) interface 40 can be provided to which the determined vital sign 39 can be delivered, e.g. to provide output data 41 for further analysis and/or for display measures. Both interfaces 32, 40 can be embodied by the same (hardware) connectors.

In an embodiment a controller 42 is provided for selectively controlling at least one of the imaging unit 28 and the radiation source 22.

The analyzer 34, the processor 36 and the post-processor 38 (and, if provided, the controller 42) may be implemented by a common processing unit 50 which can be considered a computing device, or at least, part of a computing device driven by respective logic commands (program code) so as to provide for desired data processing. The processing unit 50 may comprise several components or units which are addressed in the following. It should be understood that each component or unit of the processing unit 50 can be implemented virtually or discretely. For instance, the processing unit 50 may comprise a number of processors, such as multi-core processors or single-core processors. At least one processor can be utilized by the processing unit 50. Each of the processors can be configured as a standard processor (e.g., central processing unit) or as a special purpose processor (e.g., graphics processor). Hence, the processing unit 50 can be suitably operated so as to distribute several tasks of data processing to adequate processors.

The processing unit 50 as well as the interfaces 32, 40 can be embodied in a common processing apparatus or housing, generally representing the proposed device 30. The imaging unit 28 and the radiation source 22 are generally external elements, but may also be integrated into the device 30, e.g. with a common housing with the other elements of the device 30.

In the following, details of the background of the present invention and of preferred embodiments shall be explained.

Usually, known contact or contactless sensors for measurement of vital signs apply a post-processing algorithm to the measured vital signals, to reduce artefacts and/or improve the consistency of measurements. Most of the known 1D post-processing algorithms are controlled by information acquired either from the 1D signal itself or from additional (context) sensors. For instance, wearable contact PPG sensors (e.g. wrist or finger sensors) make use of data from an embedded accelerometer to reduce motion artefacts in the 1D vital sign information signal.

One option would be to post-process an extracted vital sign information signal, e.g. a heartbeat signal, based on information about the frequency of the repetitive motion of a subject. Such information can be acquired either from motion vectors or other data, which describe the repetitive motion of a subject. While significantly improving the robustness of heartbeat monitoring during regular motion of a subject, that method does not provide a significant improvement in case a motion of a subject is not regular. For example, if a subject suddenly turns his or her face away from the camera, an extracted heartbeat signal would be lost, and the post-processing algorithm, which relies on detection of repetitive periodic motion, would not improve the consistency of the extracted signal.

Moreover, different types of motion have different impact on quality of the extracted PPG signal. For instance, translational motion of a face, when the same skin area is constantly visible, creates much less artefacts (if any) compared to rotational motion of a face with the same frequency and speed; for rotational motion the visible skin area is constantly changing.

Yet another example when the use of motion frequency information is not optimal is the measurement of a vital sign information signal (particularly related to a heartbeat signal) (sometimes also called PPG signal) from a talking face. In this case, the majority of motion vectors would not indicate significant motion, but face skin deformation caused by talking would introduce significant artefacts in the extracted vital sign information signal.

The proposed device and method is more efficient in reduction of artefacts caused by skin motion and more responsive to the different types of motion. The improvement of the extracted vital sign is particularly based on the analysis of the temporal consistency and/or spatial smoothness of the skin area used for extraction of a vital sign.

In camera-based vital sign monitoring systems, minor color variations of skin area (e.g. face of a person), caused by blood volume changes are measured, and the vital sign information signal is extracted. The color variations are extremely small, which means that any disturbance (motion, illumination changes) would influence the signal. Motion of a monitored subject causes spatial displacement and change of the skin area. The level of artefacts caused by displacement and deformation can be largely different. Spatial displacement of the skin area without deformation (e.g. during lateral motion) is less problematic for extraction of the heart beat signals compared to deformation of the skin area. In most of the cases, artefacts caused by skin area displacement can be compensated and the residual artefacts from regular displacement of skin area can be successfully addressed during a post-processing by removing the motion spectrum from the spectrum of the measured vital sign information signal.

Artefacts caused by skin area deformation are typically much more severe (depending on the amount of deformation), and they are much more difficult to compensate. During the skin deformation, the amount of skin pixels in the sensing area varies, while the most of skin area might stay still. Therefore, analysis of motion vectors of a skin area is not sufficient for compensation of artefacts.

Moreover, the strength of the extracted vital sign information signal and its SNR is not equal over a skin area. There are some parts of the skin area which generate more noisy signals than other parts. For instance, areas with smooth skin will have a cleaner vital sign information signal, compared to skin areas with high texture. Therefore, deformation of initially smooth area with a strong vital sign information signal will create much larger (changes in) artefacts than deformation of textured areas, which already had poor vital sign information signals.

In an embodiment of the present invention it is proposed to analyse spatial and temporal properties of a skin area, and use the results of this analysis to adapt the processing of the data signals of the skin pixel areas of the skin area and/or the post-processing of an extracted vital signal information signal. Preferably, a metric for reliability of the measurements is generated as well.

Figure 2:
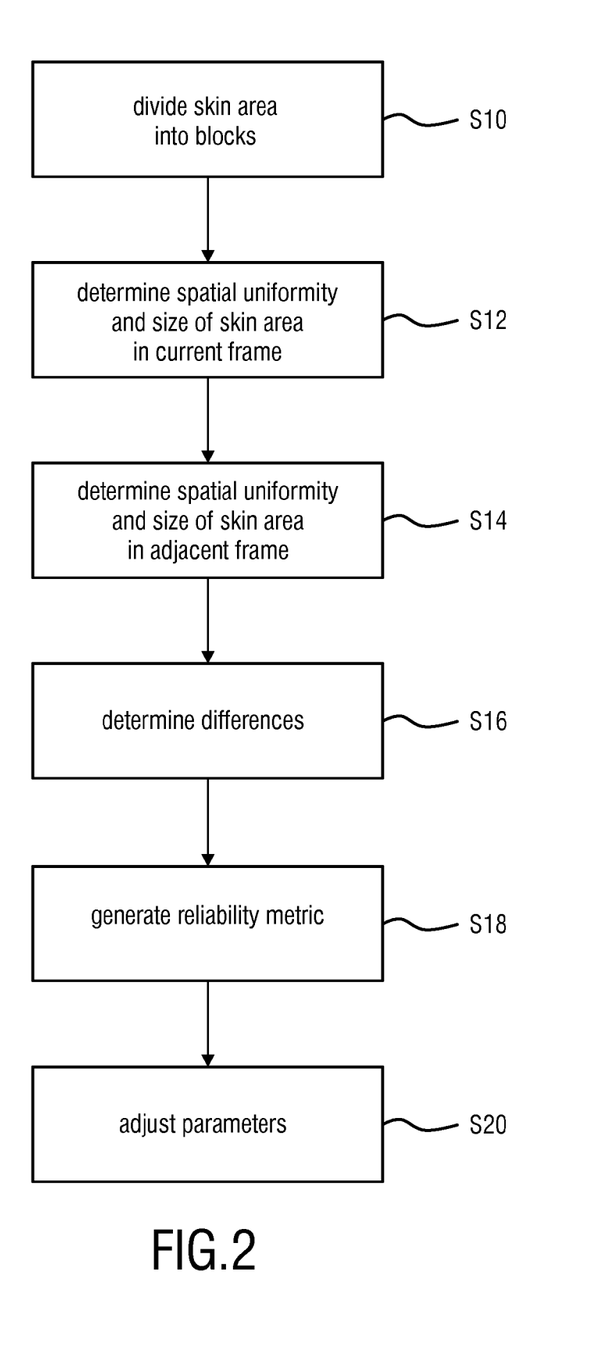
FIG. 2 shows a flowchart of an embodiment of a method according to the present invention.

FIG. 2 shows a flowchart of an embodiment of a method according to the present invention. In a first step S10 the skin area of the region of interest 14 is divided in the current and adjacent image frames into 2D blocks of pixels (also called skin pixel blocks herein). In a second step S12 the spatial uniformity of a plurality (preferably of each) of the blocks is determined and the size of the skin area is determined for the current frame. Further, the number of "smooth" and "textured" spatial blocks is determined. The uniformity can be measured using several methods, e.g. using entropy and/or dynamic range. An example of such a method is described in "Spatial Texture Analysis: A comparative Study", Maneesha Singh and Sameer Singh, PANN Research, Department of Computer Science, University of Exeter, ICPR '02 Proceedings of the 16th International Conference on Pattern Recognition (ICPR'02) Volume 1-Volume 1, Page 10676, IEEE Computer Society Washington, D.C., USA.

In a third step S14 the spatial uniformity and the size of the skin area in the adjacent image frame is determined. In a fourth step S16 the differences between the sizes of the skin area in the considered image frames and the change of the number of "smooth" and "textured" blocks are determined.

In a fifth step S18 a reliability metric is generated based on the parameters of temporal and spatial stability with the following qualitative relation: The larger the difference in the size of the total skin areas, and in the number of the "smooth" blocks, the less reliable is the extracted vital sign information signal or the vital sign (e.g. heartbeat of respiration). The larger the number of "smooth" blocks in the skin area, the higher the reliability of the extracted vital sign information signal or the vital sign.

In a sixth step S20 the parameters of the post-processing are adjusted based on the results of the analysis at step S18. For instance, a temporal window (or time constant) of a low-pass filter can be increased to reduce fluctuations of the extracted vital sign information signal or vital sign. Alternatively, the width of a bandpass filter applied to the extracted vital sign information signal or vital sign can be reduced or/and shifted around the previously reliable value. Yet another alternative is that the previous output of the post-processor can be preserved when the reliability metric (from step S18) showed a high reliability for the previous value and a low reliability for the current one. The value can be adjusted next time only when the reliability metric shows that the extracted vital sign information signal or vital sign is reliable again.

As a result of the above processing, the fluctuations of the extracted signal are reduced if the skin area is not spatially and temporally stable.

Instead of adjusting the post-processor 38, the reliability measure (or the underlying analysis) can be used at other stages of the processing as well, as is clear from the following embodiments.

In another embodiment of the present invention, all blocks in the skin area are ranked depending on their temporal stability and the skin blocks with highest temporal instability are completely removed or ignored from the sensing area (i.e., no signal is extracted and/or used from those blocks for determining the desired vital sign).

In yet another embodiment of the present invention, a similar approach can be used to weigh the contribution of separate spatial blocks of the skin area for the final signal. Parts of the skin area for which, based on the discussed measures, it is expected that a relatively low number of artefacts is generated, are given more weight than others.

In yet another embodiment of the present invention it is proposed to include the analysis of color and/or intensity stability of blocks in adjacent image frames (e.g. changes of the average value of chrominance or/and luminance of blocks between adjacent image frames). If the number of blocks with changes of the average value of chrominance or/and luminance is above a certain level, then the determined vitals sign is not reliable. The reliability metric is adapted accordingly (e.g. in step S16 of the embodiment explained in FIG. 2).

By way of example, the present invention can be applied in the field of health care, e.g. unobtrusive remote patient monitoring, general surveillances, security monitoring and so-called lifestyle environments, such as fitness equipment, or the like. Applications may include monitoring of oxygen saturation (pulse oximetry), heart rate, blood pressure, cardiac output, changes of blood perfusion, assessment of autonomic functions, and detection of peripheral vascular diseases.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or an does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

As used herein, the term "computer" stands for a large variety of processing devices. In other words, also mobile devices having a considerable computing capacity can be referred to as computing device, even though they provide less processing power resources than standard desktop computers. Furthermore, the term "computer" may also refer to a distributed computing device which may involve or make use of computing capacity provided in a cloud environment.

Furthermore, the different embodiments can take the form of a computer program product accessible from a computer usable or computer readable medium providing program code for use by or in connection with a computer or any device or system that executes instructions. For the purposes of this disclosure, a computer usable or computer readable medium can generally be any tangible device or apparatus that can contain, store, communicate, propagate, or transport the program for use by or in connection with the instruction execution device.

In so far as embodiments of the disclosure have been described as being implemented, at least in part, by software-controlled data processing devices, it will be appreciated that the non-transitory machine-readable medium carrying such software, such as an optical disk, a magnetic disk, semiconductor memory or the like, is also considered to represent an embodiment of the present disclosure.

The computer usable or computer readable medium can be, for example, without limitation, an electronic, magnetic, optical, electromagnetic, infrared, or semiconductor system, or a propagation medium. Non-limiting examples of a computer readable medium include a semiconductor or solid state memory, magnetic tape, a removable computer diskette, a random access memory (RAM), a read-only memory (ROM), a rigid magnetic disk, and an optical disk. Optical disks may include compact disk-read only memory (CD-ROM), compact disk-read/write (CD-R/W), and DVD.

Further, a computer usable or computer readable medium may contain or store a computer readable or usable program code such that when the computer readable or usable program code is executed on a computer, the execution of this computer readable or usable program code causes the computer to transmit another computer readable or usable program code over a communications link. This communications link may use a medium that is, for example, without limitation, physical or wireless.

A data processing system or device suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories, which provide temporary storage of at least some computer readable or computer usable program code to reduce the number of times code may be retrieved from bulk storage during execution of the code.

Input/output, or I/O devices, can be coupled to the system either directly or through intervening I/O controllers. These devices may include, for example, without limitation, keyboards, touch screen displays, and pointing devices. Different communications adapters may also be coupled to the system to enable the data processing system to become coupled to other data processing systems, remote printers, or storage devices through intervening private or public networks. Non-limiting examples are modems and network adapters and are just a few of the currently available types of communications adapters.

The description of the different illustrative embodiments has been presented for purposes of illustration and description and is not intended to be exhaustive or limited to the embodiments in the form disclosed. Many modifications and variations will be apparent to those of ordinary skill in the art. Further, different illustrative embodiments may provide different advantages as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated. Other variations to the disclosed embodiments can be understood and effected by those skilled in the art in practicing the claimed invention, from a study of the drawings, the disclosure, and the appended claims.

The invention claimed is:

1. A device configured to determine a vital sign of a subject, the device comprising:
   an interface configured to receive a data stream derived from detected electromagnetic radiation reflected from a region of interest including a skin area of the subject, said data stream comprising a data signal per skin pixel area of one or more skin pixels for a plurality of skin pixel areas of said region of interest, the data signal representing the detected electromagnetic radiation reflected from the respective skin pixel area over time,
   an analyzer configured to analyze spatial and/or temporal properties of the skin area, and configured to determine reliability information from said spatial and/or temporal properties of the skin areas, said reliability information indicating the reliability of the determination of the vital sign information or vital sign determined based on the data signals of skin pixel areas within the skin area;

a processor configured to determine a vital sign information signal of the subject based on the data signals of skin pixel areas within the skin area, and a post-processor configured to determine the desired vital sign from said vital sign information signal, wherein said determined spatial and/or temporal properties and said reliability information are used by the processor for determining the vital sign information signal and/or by the post-processor for determining the desired vital sign.

2. The device as claimed in claim 1,
wherein said analyzer is configured to determine the smoothness, size, uniformity of the skin area and/or of chrominance and/or luminance components of the skin area over time.

3. The device as claimed in claim 1,
wherein said analyzer is configured to determine the spatial uniformity the skin area over time by dividing the skin area into skin pixel blocks, determining the spatial uniformity of said skin pixel blocks and determining the number of smooth and/or textured smooth skin pixel blocks.

4. The device as claimed in claim 3,
wherein said analyzer is configured to determine the number of smooth and/or textured smooth skin pixel blocks over time.

5. The device as claimed in claim 4,
wherein said analyzer is configured to determine said reliability information using the change of the number of smooth and/or textured smooth skin pixel blocks over time and/or the change of a size of the skin area over time.

6. The device as claimed in claim 5,
wherein said analyzer is configured to determine the reliability information to indicate a higher reliability the higher the number of smooth skin pixel blocks and larger the size of the skin area.

7. The device as claimed in claim 1,
wherein said post-processor is configured to set a temporal width and/or a time constant of a low-pass filter of said post-processor based on said determined spatial and/or temporal properties.

8. The device as claimed in claim 1,
wherein said post-processor is configured to set a width of a band-pass filter of said post-processor based on said determined spatial and/or temporal properties.

9. The device as claimed in claim 1,
wherein said post-processor is configured to update the determined vital sign only if the reliability information indicates a reliability above a predetermined reliability threshold.

10. The device as claimed in claim 1,
wherein said processor is configured to rank skin pixel blocks of the skin area according to their associated temporal stability and to determine a vital sign information signal of the subject based on the data signals of skin pixels from the most temporally stable skin pixel blocks within the skin area.

11. The device as claimed in claim 1,
wherein said processor is configured to determine reliability weights for skin pixel blocks of the skin area according to their associated temporal stability and to determine a vital sign information signal of the subject based on the data signals of skin pixels, which are weighted according to the determined reliability weights of the associated skin pixel blocks.

12. A non-transitory computer readable medium having instructions stored thereon which, when carried out on a computer, cause the computer to perform a method for determining a vital sign of a subject, the method comprising:
receiving a data stream derived from detected electromagnetic radiation reflected from a region of interest including a skin area of the subject, said data stream comprising a data signal per skin pixel area of one or more skin pixels for a plurality of skin pixel areas of said region of interest, the data signal representing the detected electromagnetic radiation reflected from the respective skin pixel area over time, analyzing spatial and/or temporal properties of the skin area, determine reliability information from said spatial and/or temporal properties of the skin area, said reliability information indicating the reliability of the determination of the vital sign information or vital sign determined based on the data signals of skin pixel areas within the skin area;

determining a vital sign information signal of the subject based on the data signals of skin pixel areas within the skin area, determining the desired vital sign from said vital sign information signal, and determining the vital sign information signal and/or the desired vital sign from said determined spatial and/or temporal properties.

13. A device configured to determine a vital sign of a subject, the device comprising:
an interface configured to receive a data stream derived from detected electromagnetic radiation reflected from a region of interest including a skin area of the subject, said data stream comprising a data signal per skin pixel area of one or more skin pixels for a plurality of skin pixel areas of said region of interest, the data signal representing the detected electromagnetic radiation reflected from the respective skin pixel area over time, at least one computer processor programmed to:
analyze at least one of spatial and temporal properties of the skin area, and configured to determine reliability information from said spatial and/or temporal properties of the skin area, said reliability information indicating the reliability of the determination of the vital sign information or vital sign determined based on the data signals of skin pixel areas within the skin area;

determine a vital sign information signal of the subject based on the data signals of the analyzed at least one spatial and temporal properties and the reliability information, and determine a vital sign from said vital sign information signal.

14. The device as claimed in claim 13, wherein the at least one processor is further programmed to:
determine at least one of a smoothness, size, uniformity of the skin area and/or of chrominance and/or luminance components of the skin area over time.

15. The device as claimed in claim 13, wherein the at least one computer processor is further programmed to:
determine a spatial uniformity the skin area over time by dividing the skin area into skin pixel blocks, determining the spatial uniformity of said skin pixel blocks and determining the number of smooth and/or textured smooth skin pixel blocks.

16. The device as claimed in claim 15, wherein the at least one computer processor is further programmed to:
determine the number of smooth and/or textured skin pixel blocks over time, using the change of the number of smooth and/or textured smooth skin pixel blocks over time and or the change of the size of the skin area over time.

17. The device as claimed in claim 13, wherein the at least one computer processor is further programmed to:
set at least one of a temporal width and a time constant of a low-pass filter based on said determined spatial and/or temporal properties.

18. The device as claimed in claim 13, wherein the at least one computer processor is further programmed to:
update the determined vital sign only if the reliability information indicates a reliability above a predetermined reliability threshold.

19. The device as claimed in claim 13, wherein the at least one computer processor is further programmed to:
rank skin pixel blocks of the skin area according to their associated temporal stability; and
determine a vital sign information signal of the subject based on the data signals of skin pixels from the most temporally stable skin pixel blocks within the skin area.

20. The device as claimed in claim 13, wherein the at least one computer processor is further programmed to:
determine reliability weights for skin pixel blocks of the skin area according to their associated temporal stability; and
determine a vital sign information signal of the subject based on the data signals of skin pixels weighted with the determined reliability weights of the associated skin pixel blocks.

* * * * *